United States Patent [19]

Connor et al.

[11] 4,009,261
[45] Feb. 22, 1977

[54] 7-SUBSTITUTED TRIOL DERIVATIVES OF ACID S, AN ANTIBIOTIC PRODUCED BY POLYANGIUM CELLULOSUM VAR. FULVUM

[75] Inventors: David T. Connor, Parsippany; Samuel M. Ringel, Rockaway; Maximilian von Strandtmann, Rockaway Township, all of N.J.

[73] Assignee: Warner-Lambert Company, Morris Plains, N.J.

[22] Filed: Aug. 7, 1975

[21] Appl. No.: 602,606

[52] U.S. Cl. .............................. 424/121; 424/122
[51] Int. Cl.$^2$ ................................... A61K 35/74
[58] Field of Search .......................... 424/122, 121

[56] References Cited

UNITED STATES PATENTS 3,804,948  4/1974  Stvandtmann et al. ............ 424/122

Primary Examiner—Jerome D. Goldberg
Attorney, Agent, or Firm—Albert H. Graddis; Frank S. Chow; Anne M. Kelly

[57] ABSTRACT

The present invention relates to 7-substituted triol derivatives of the novel antibiotic substance, acid S, produced by the organism *Polyangium cellulosum* var. *fulvum* (ATCC No. 25532) and to processes for their preparation. The 7-substituted triol derivatives of acid S of this invention are useful as antifungal agents.

3 Claims, 3 Drawing Figures

7-ETHYLTRIOL S

7-PHENYLTRIOL S

7-SUBSTITUTED TRIOL DERIVATIVES OF ACID S, AN ANTIBIOTIC PRODUCED BY *POLYANGIUM CELLULOSUM* VAR. *FULVUM*

SUMMARY OF THE INVENTION

The present invention relates to novel 7-substituted triol derivatives of acid S, a potent antibiotic produced by fermentation of the microorganism *Polyangium cellulosum* var. *fulvum* (ATCC No. 25532) in an appropriate culture medium. Specifically, the present invention relates to structural modifications of acid S having the following formula:

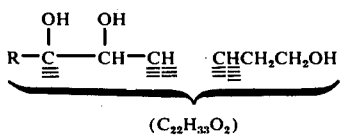

$(C_{22}H_{33}O_2)$ wherein R is 1 to 7 carbon lower alkyl, preferably 1 to 4 carbon lower alkyl; or aryl, such as phenyl or naphthyl. $C_{22}H_{33}O_2$ represents the remaining part of the molecule.

BRIEF DESCRIPTION OF THE DRAWINGS

The infrared spectra of representative 7-substituted triol derivatives of this invention are illustrated in FIGS. 1, 2 and 3 of the drawings.

Figure 1:
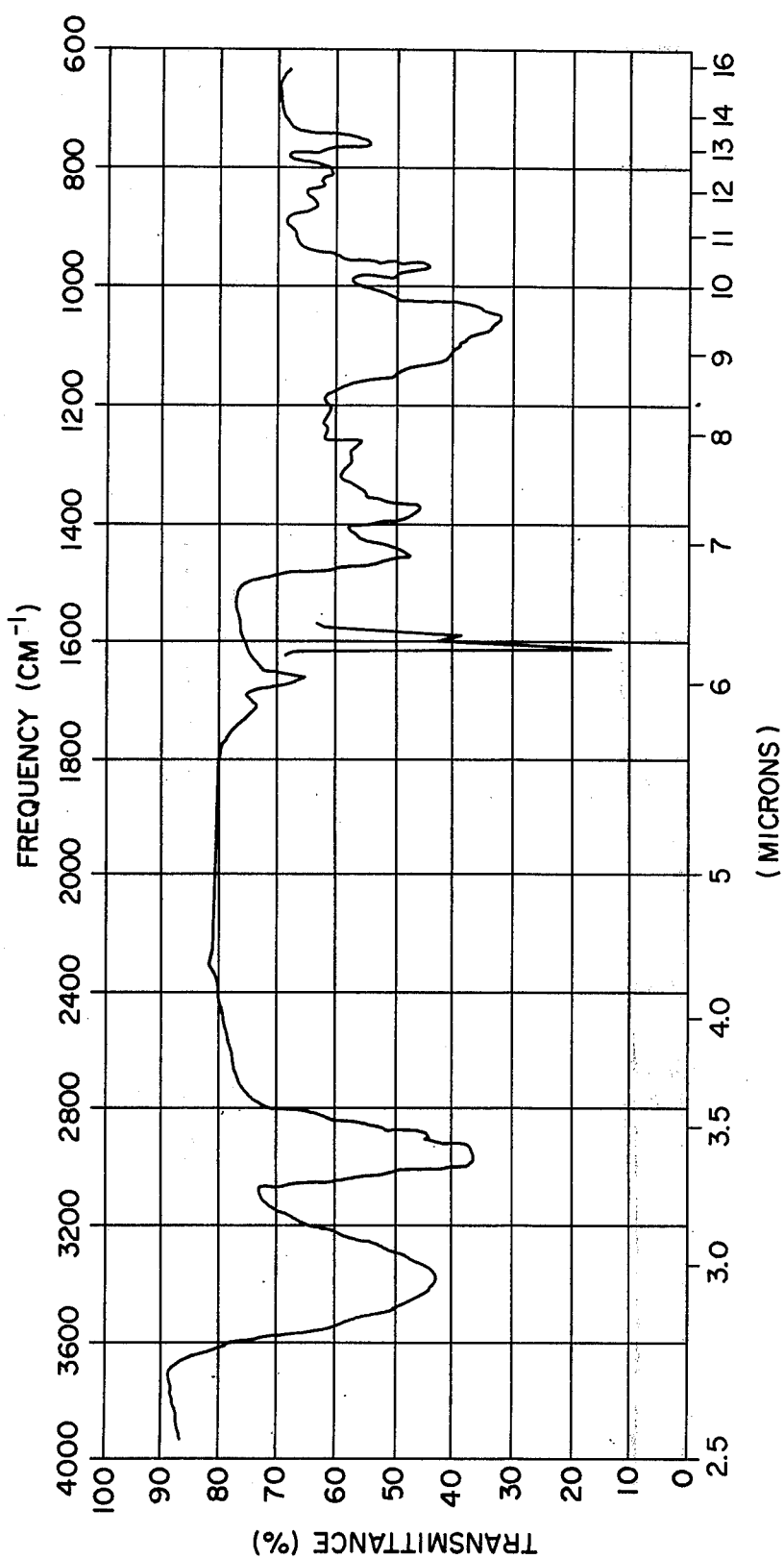
FIG. 1 depicts the infrared spectrum of 7-methyltriol S.

The novel 7-substituted triols of this invention are prepared from the antibiotic substance ketodiol S, which is described in U.S. Ser. No. 482,052, filed June 24, 1974, now U.S. Pat. No. 3,932,620. Ketodiol S is prepared from the antibiotic substance Triol S, described in U.S. Ser. No. 482,054, filed June 24, 1974, now U.S. Pat. No. 3,932,621, which in turn is obtained from the antibiotic substance acid S and its corresponding methyl ester by reductive modification of the acid or ester groups of acid S and S methyl ester.

Acid S, as disclosed in U.S. Pat. No. 3,651,216, issued Mar. 21, 1972 and U.S. Pat. No. 3,804,948, issued Apr. 16, 1974, is a potent antifungal substance, elaborated when the microorganism *Polyangium cellulosum* var. *fulvum* (ATTC No. 25532) is fermented in a suitable culture medium. The aforementioned patent (U.S. Pat. No. 3,804,948) also describes the chemical preparation of the methyl ester of acid S.

The organism designated *Polyangium cellulosum* var. *fulvum* is deposited at the American Type Culture Collection, and identified as ATCC No. 25532. All restriction on the availability of the culture deposit at ATCC will be irrevocably removed upon issuance of the instant application. The culture at ATCC will be maintained throughout the effective life of the patent.

Thus, according to this invention, novel 7-substituted triols of acid S may be prepared reacting one equivalent of acid S with from about 3 to about 25 equivalents (preferably about 10 equivalents) of lithium aluminum hydride, in a sufficient amount of solvent to allow proper refluxing action, for about 3 hours. Typically, from about 100 to about 1000 equivalents of refluxing ether or tetrahydrofuran are used. This reaction provides triol S ($C_{28}H_{44}O_5$) which is isolated.

One equivalent of triol S is reacted with from about 15 to about 25 equivalents of silver carbonate-on-celite in a sufficient amount of refluxing toluene to allow proper refluxing action. Typically, from about 100 to about 200 equivalents of toluene are used. This reaction provides ketodiol S ($C_{28}H_{42}O_5$), which is isolated.

One equivalent of ketodiol S is treated with from about 5 to about 20 equivalents, preferably about 10 equivalents of an alkyl or aryl magnesium halide, i.e., magnesium chloride, iodide or bromide, preferably magnesium bromide, in a sufficient amount of refluxing solvent to allow proper refluxing action for about 3 hours. Typically, from about 200 to about 500 equivalents of anhydrous ether or tetrahydrofuran are used. Thus, one obtains the novel 7-substituted triol derivatives of acid S of this invention: the 7-position of the triol S is selectively oxidized to obtain the corresponding ketodiol, which is subjected to alkylation. The alkylation takes place on the oxidized 7-position and novel 7-substituted triols are obtained.

The compounds of the present invention are characterized by infrared spectroscopy and mass spectrometry. The infrared spectra of the 7-substituted triol derivatives of acid S of this invention are determined as thin films with an infrared absorption spectrometer equipped with a diffraction grating. In addition to providing spectral evidence for the chemical transformations of the processes of this invention, the infrared spectra of the compounds of this invention represent characteristic physical properties useful for their identification.

The mass spectra of the 7-substituted keto triol derivatives of acid S of this invention are measured on a double-focusing high resolution mass spectrometer utilizing a heated direct insertion probe. The molecular composition of the parent peaks are determined by employing perfluorotributylamine (mass spectral grade, available from PCR, Inc., Gainsville, Florida) as the internal standard and peak matching techniques well-known to those skilled in the art. The application of these mass spectral techniques permits not only the determination of the molecular composition of the parent ion and confirmation of the postulated transformations, but, like the aforementioned infrared measurements, provides a definitive physical property useful for identification purposes.

The novel 7-substituted triol derivatives of this invention inhibit the growth of fungi, such as of yeast phase of *Histoplasma capsulatum*, and *Microsporum fulvum*. Minimum inhibitory concentrations falling within the range of 6.25 to 0.78 micrograms/milliliter, are obtained when evaluated by the in vitro tube dilution technique described in U.S. Pat. No. 3,651,216. Thus, the compounds of the present invention are useful for the treatment of dermatophytic and systemic fungal disease.

The antifungal substances of this invention can be formulated with inert excipients into various dosage forms for oral, parenteral and topical administration by methods well-known to those skilled in the pharmacist's art. Tablets, capsules, powders, solutions, suspensions, ointments, gels and creams are included among these dosage forms.

The 7-substituted triol derivatives of acid S of this invention can be administered orally, parenterally or topically to various mammals, such as dogs, cats and guinea pigs, afflicted with fungal disease. The typical dose is about 0.01 to 100 mg/kg of body weight of the animal.

The following examples are included to further illustrate the invention and are not to be construed as limiting the scope of the invention:

EXAMPLE I

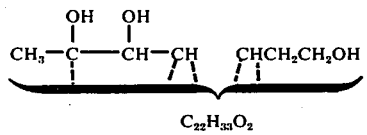

7-Methyltriol S.

A solution of keto diol S (20mg) and a large excess of methyl magnesium bromide (10 equivalents) in anhydrous ether (20ml) are refluxed under nitrogen for 3 hours. The reaction mixture is extracted with ether and then with chloroform. The extracts are combined, dried over $MgSO_4$ and evaporated under reduced pressure to give a colorless oil (20mg). The product is purified by preparative thin layer chromatography to give a colorless oil (13mg 63%). Thin layer chromatography indicates a pure homogeneous product.
Empirical formula, $C_{29}H_{46}O_5$.
 Molecular weight, 474.7.
 Infrared Spectrum, $\nu$ max 3500–3200cm$^{-1}$.
 Mass Spectrum.
  Observed molecular ion 474.3290
  Calculated for $C_{29}H_{46}O_5$ 474.3345
m/e (relative intensity) 474 (8), 456 (8), 445 (10), 438 (4), 379 (2), 361 (6), 279 (100), 193 (50) and 165 (52).

EXAMPLE II

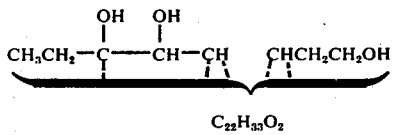

7-Ethyltriol S.

Prepared from keto diol S (15mg) and ethyl magnesium bromide (10 equivalents) by the general method described in Example I. The product is purified by preparative tlc to give a pale yellow oil (2mg 12%). Diagnostic tlc indicated a pure homogeneous product.
Empirical formula, $C_{30}H_{48}O_5$.
 Molecular weight, 488.7.
 Infrared Spectrum, $\nu$ max 3500–3200cm$^{-1}$.
 Mass Spectrum.
  Observed molecular ion 488.3499
  Calculated for $C_{30}H_{48}O_5$ 488.3502
m/e (relative intensity) 488 (22), 470 (18), 459 (54), 393 (13), 293 (54), 193 (100).

EXAMPLE III

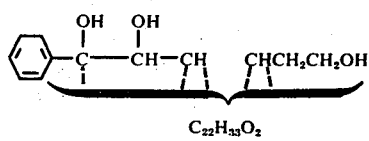

7-Phenyltriol S.

Prepared from ketodiol S (50mg) and phenyl magnesium bromide (10 equivalents) by the general method described in Example I. The product is purified by preparative tlc to give a pale yellow oil (8mg 15%). Diagnostic tlc indicates a pure homogeneous product.
Empirical formula, $C_{34}H_{48}O_5$.
 Molecular weight, 536.7.
 Infrared Spectrum, $\nu$ max 3500–3200cm$^{-1}$.
 Mass Spectrum.
  Observed molecular ion 536.3585
  Calculated for $C_{34}H_{48}O_5$ 536.3502
m/e (relative intensity) 536 (23), 518 (19), 507 (10), 500 (8), 341 (83), 323 (16), 244 (26), 236 (43), 195 (77), 193 (77) and 177 (100).

We claim:
1. An antifungal substance, 7-methyltriol S, having the following characteristics:
 Empirical formula: $C_{29}H_{46}O_5$
 Molecular weight: 474.7
 Infrared Spectrum as shown in FIG. 1: $\nu$ max 3500–3200cm$^{-1}$
 Mass Spectrum:
  Observed molecular ion 474.3290
  Calculated for $C_{29}H_{46}O_5$ 474.3345
m/e (relative intensity) 474 (8), 456 (8), 445 (10), 438 (4), 379 (2), 361 (6), 279 (100), 193 (50) and 165 (52).

Figure 2:
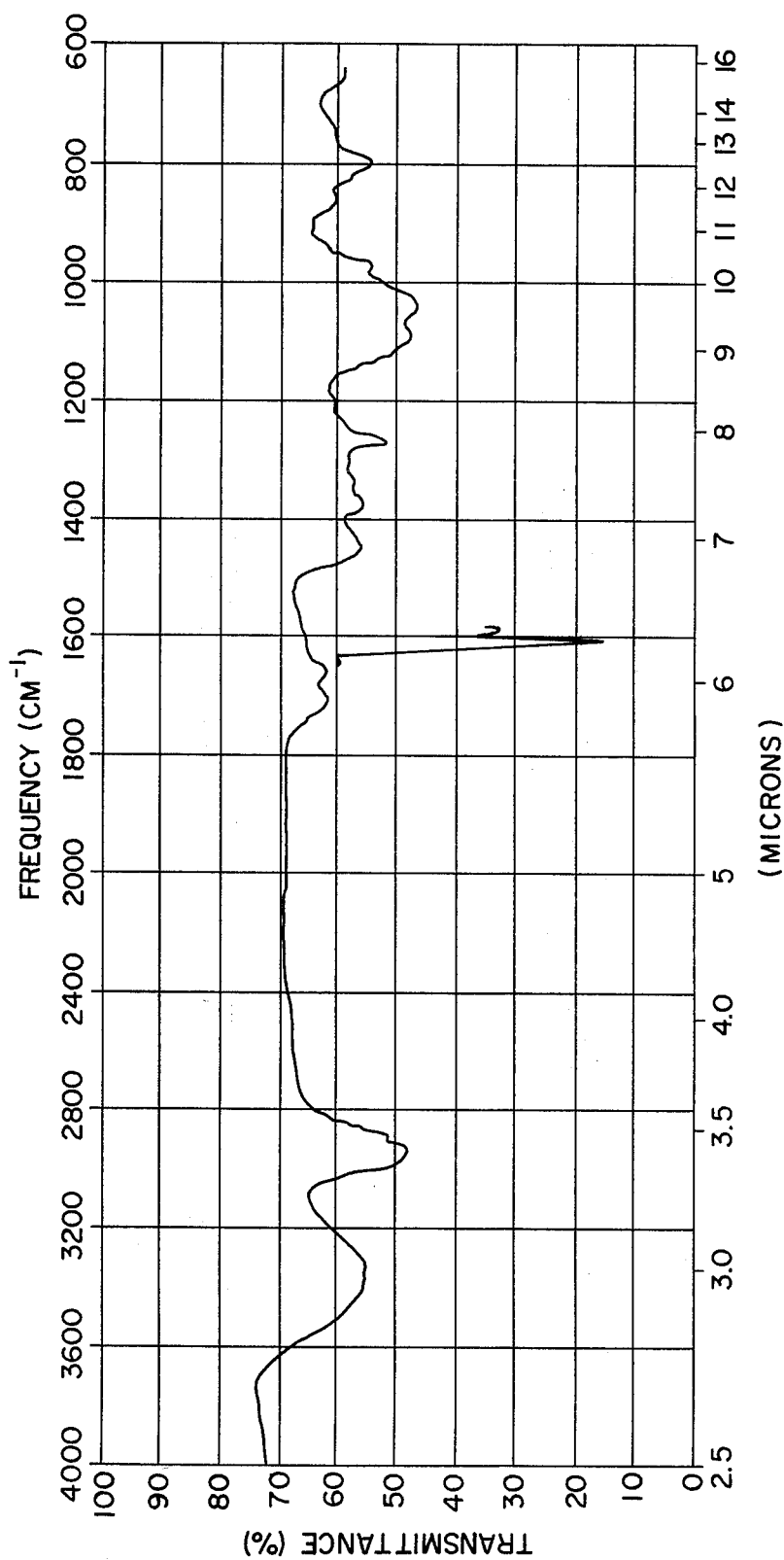
FIG. 2 depicts the infrared spectrum of 7-ethyltriol S.

2. An antifungal substance, 7-ethyltriol S, have the following characteristics:
 Empirical formula: $C_{30}H_{48}O_5$
 Molecular weight: 488.7
 Infrared Spectrum as shown in FIG. 2: $\nu$ max 3500–3200cm$^{-1}$
 Mass Spectrum:
  Observed molecular ion 488.3499
  Calculated for $C_{30}H_{48}O_5$ 488.3502
m/e (relative intensity) 488 (22), 470 (18), 459 (54), 393 (13), 293 (54) and 193 (100).

Figure 3:
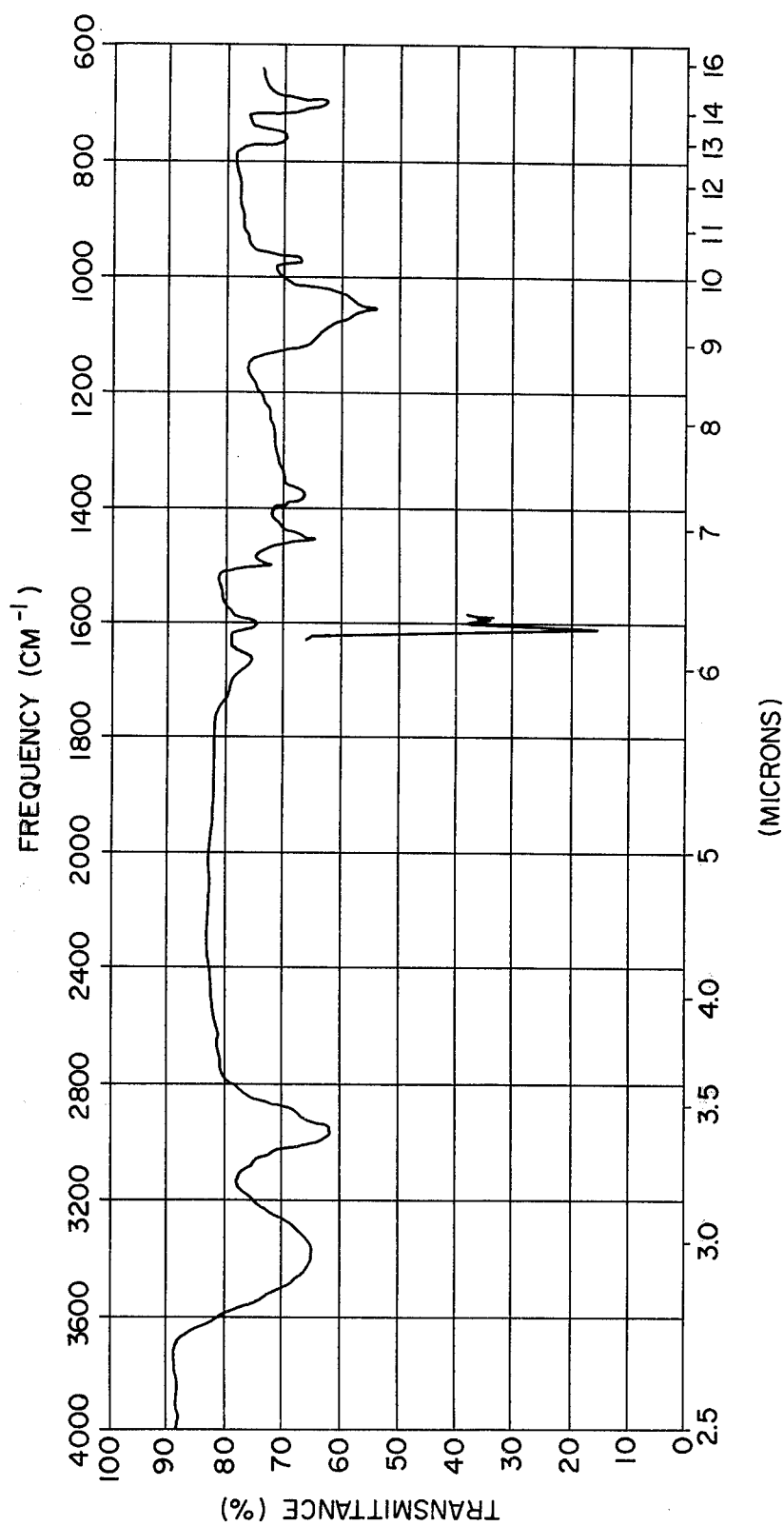
FIG. 3 depicts the infrared spectrum of 7-phenyltriol S.

3. An antifungal substance, 7-phenyltriol S, having the following characteristics:
 Empirical formula: $C_{34}H_{48}O_5$
 Molecular weight: 536.7
 Infrared Spectrum as shown in FIG. 3: $\nu$ max 3500–3200cm$^{-1}$
 Mass Spectrum:
  Observed molecular ion 536.3585
  Calculated for $C_{34}H_{48}O_5$ 536.3502
m/e (relative intensity) 536 (23), 518 (19), 507 (10), 500 (8), 341 (83), 323 (16), 244 (26), 236 (43), 195 (77), 193 (77) and 177 (100).

* * * * *